United States Patent [19]

Collier

[11] Patent Number: 4,560,813
[45] Date of Patent: Dec. 24, 1985

[54] PROCESSES FOR THE PRODUCTION OF ALKYLENE GLYCOL IN THE PRESENCE OF ORGANOMETALATE

[75] Inventor: Joseph A. Collier, S. Charleston, W. Va.

[73] Assignee: Union Carbide Corporation, Danbury, Conn.

[21] Appl. No.: 594,269

[22] Filed: Mar. 28, 1984

[51] Int. Cl.[4] .................... C07C 29/76; C07C 31/20; C07C 31/27; C07C 33/26
[52] U.S. Cl. ................................ 568/872; 568/810; 568/811; 568/833; 568/857; 568/867
[58] Field of Search ............... 568/867, 872, 833, 810, 568/811, 857

[56] References Cited

U.S. PATENT DOCUMENTS 2,615,901 10/1952 McClellan .......................... 568/867
4,277,632 7/1981 Kumazawa et al. ................ 568/857

FOREIGN PATENT DOCUMENTS 73035 6/1981 Japan ................................. 568/867
595407 12/1947 United Kingdom ................ 568/872

OTHER PUBLICATIONS

U.S. patent application Ser. No. 594,268, filed 3/28/84.

Primary Examiner—J. E. Evans
Attorney, Agent, or Firm—Norman L. Balmer

[57] ABSTRACT

In processes for making alkylene glycols by the hydrolysis of alkylene oxides in the presence of selectivity-enhancing metalate anion-containing material, metalate anion can be recovered from the alkylene glycol-containing hydrolysis product by contact with a solid having electropositive complexing sites thereon such as anion exchange resins.

22 Claims, 1 Drawing Figure

PROCESSES FOR THE PRODUCTION OF ALKYLENE GLYCOL IN THE PRESENCE OF ORGANOMETALATE

This invention relates to processes for the production of alkylene glycols, particularly monoalkylene glycols, from alkylene oxides and water in the presence of a metalate anion-containing material. Advantageously, the processes of this invention enable the recovery and reuse of the metalate anion in a commercially-attractive manner and without undue deterioration of the metalate anion.

INTRODUCTION TO THE HYDROLYSIS OF ALKYLENE OXIDE USING METALATE ANION

Commercial processes for the preparation of alkylene glycols, for example, ethylene glycol, propylene glycol and butylene glycol, involve the liquid-phase hydration of the corresponding alkylene oxide in the presence of a large molar excess of water (see, for example, Kirk-Othmer, *Encyclopedia of Chemical Technology*, Vol. 11, Third Edition, page 939 (1980)). The hydrolysis reaction is typically conducted at moderate temperatures, e.g., about 100° C. to about 200° C., with water being provided to the reaction zone in excess of 15 moles per mole of alkylene oxide. The primary by-products of the hydrolysis reaction are di- and polyglycols, e.g., dialkylene glycol, trialkylene glycol and tetra-alkylene glycol. The formation of the di- and polyglycols is believed to be primarily due to the reaction of alkylene oxide with alkylene glycol. As alkylene oxides are generally more reactive with alkylene glycols than they are with water, the large excesses of water are employed in order to favor the reaction with water and thereby obtain a commercially-attractive selectivity to the monoglycol product.

Since the alkylene glycols must be recovered from the hydrolysis reaction mixtures, the large excess of water can result in an energy intensive procedure. Typically, the water is removed by evaporation to leave an alkylene glycol-containing residue which is purified by distillation. Hence, a reduction in the amount of water employed while maintaining, or enhancing, selectivity toward the monoglycol product could be beneficial from the standpoint of energy efficiency.

Not only is the monoglycol product often the desired product for the hydrolysis of alkylene oxides but also many of the applications for monoglycols are demanding in the quality of the monoglycol product. For instance, monoethylene glycol is used in the preparation of polyesters (polyethylene terephthalate) and must meet rigid standards so as not to adversely affect the properties of the finished polyesters, e.g., fiber or film. Typical polyester grade monoethylene glycol must meet the specifications set forth in Table I:

TABLE I

| Representative Polyester Grade Specifications | |
|---|---|
| Specific Gravity (20/20° C.) | 1.1151–1.1156 |
| Distillation, 760 mm | |
| Ibp, °C. min. | 196 |
| Dp, °C. max. | 200 |
| Acidity, % by wt., as HAc max. acid | 0.005 |
| UV Transmittances — Wavelength (mu) | Transmittance (%, min.) |
| 220 | 70 |
| 275 | 90 |
| 350 | 98 |
| Iron, ppm max. | 0.07 |
| Chlorides | none by test |
| Diethylene glycol, % by wt., max. | 0.08 |
| Water, % by wt., max. | 0.08 |
| Water solubility at 25° C. | miscible, all proportions |
| Ash, gm/100 ml, max. | 0.005 |
| Color, Pt-Co. max. | 5 |
| Odor | mild, practically none |
| Suspended matter | substantially free |

Accordingly, interest exists in assuring that the alkylene glycol product from the hydrolysis process can be readily refined to obtain the desired, high quality product. Any effort to enhance the yield of monoalkylene glycol, e.g., by the use of catalysts, is also viewed from the standpoint of the effect on the quality of the hydrolysis and any additional costs involved in refining the monoalkylene glycol to meet any demanding specifications for the product.

Previously, numerous catalysts have been proposed to enhance the selectivity of the hydrolysis reaction to monoalkylene glycol.

For example, U.S. Pat. No. 4,277,632, issued July 7, 1981, discloses a process for the production of alkylene glycols by the hydrolysis of alkylene oxides in the presence of a catalyst of at least one member selected from the group consisting of molybdenum and tungsten. The patent discloses that the catalyst may be metallic molybdenum or metallic tungsten, or inorganic or organic compounds thereof, such as oxides, acids, halides, phosphorous compounds, polyacids, alkali metal and alkaline earth metal, ammonium salts and heavy metal salts of acids and polyacids, and organic acid salts. An objective of the disclosed process is stated to be the hydrolysis of alkylene oxides wherein water is present in about one to five times the stoichiometric value without forming appreciable amounts of by-products such as the polyglycols. The reaction may be carried out in the presence of carbon dioxide; however, when the reaction is carried out in the presence of nitrogen, air, etc., the patentees state that the pH of the reaction mixture should be adjusted to a value in the range of 5 to 10. Japanese Kokai No. JA 54/128,507, published Oct. 5, 1979, discloses a process for the production of alkylene glycols from alkylene oxides and water using metallic tungsten and/or tungsten compounds.

Japanese Kokai No. JA 56/073,035, published June 17, 1981, discloses a process for the hydrolysis of alkylene oxide under a carbon dioxide atmosphere in the presence of a catalyst consisting of a compound containing at least one element selected from the group of titanium, zirconium, vanadium, niobium, tantalum and chromium. The compounds include the oxides, sulfides, acids, halides, phosphorous compounds, polyacids, alkali metal salts of acids and polyacids, ammonium salts of acids and polyacids, and heavy metal salts of acids.

Japanese Kokai No. JA 56/073,036, published June 17, 1981, discloses a process for the hydrolysis of alkylene oxide under a carbon dioxide atmosphere in the presence of a catalyst consisting of a compound containing at least one element selected from a group comprising aluminum, silicon, germanium, tin, lead, iron, cobalt and nickel.

U.S. patent applications Ser. Nos. 428,815, filed Sept. 30, 1982, (now abandoned) and 530,235, filed Sept. 8, 1983, of J. H. Robson and G. E. Keller, disclose the production of monoalkylene glycols with high selectivity by the reaction of a vicinal alkylene oxide with water in the presence of a water-soluble vanadate. Hence, lower water to alkylene oxide ratios can be employed using the disclosed process with attractive selectivities to the monoglycol products. The counter ion to the vanadate is selected to provide a water-soluble vanadate salt under the reaction conditions employed and alkali metals, alkaline earth metals, quaternary ammonium, ammonium, copper, zinc, and iron are suggested cations. It is also disclosed that the vanadate may be introduced into the reaction system in the salt form or on a support such as silica, alumina, zeolites and clay. Since the vanadate ion is water soluble, it can be lost from the reaction system and means must be provided to recover it from the effluent from the reaction zone.

Selectivity-enhancing metalate anions in association with organic-containing cations or electropositive complexing sites (herein referred to as organometalates) are proposed for use in the hydrolysis of alkylene oxides. Copending U.S. patent application Ser. No. 594,385, filed on even date herewith, of J. R. Briggs and J. H. Robson, is directed to processes for the hydrolysis of alkylene oxides in a reaction menstruum comprising two phases, an aqueous phase and a substantially water-insoluble phase in which the concentration of a selectivity-enhancing metalate anion-containing material (which may be an organometalate) is greater in the water-insoluble phase than in the aqueous phase. Advantageously, the alkylene glycol product is preferentially soluble in the aqueous phase and the recovery of the metalate anion-containing material from the product is facilitated by the ability to use phase separation.

Copending U.S. patent application Ser. No. 594,256, filed on even date herewith, of J. R. Briggs, G. L. O'Connor, and J. H. Robson, is directed to processes for the hydrolysis of alkylene oxides in which alkylene oxide and a selectivity enhancing, dissociatable metalate anion (which may be an organometalate) are contacted in the relative absence of water under conditions sufficient to associate at least a portion of the alkylene oxide with the metalate anion and then the associated material is contacted with water to form alkylene glycol. In embodiments of the invention, virtually all the produced alkylene glycol is monoalkylene glycol.

Copending U.S. patent application Ser. No. 594,268, filed on even date herewith, of R. D. Best, J. A. Collier, B. T. Keen and J. H. Robson, is directed to processes for the hydrolysis of alkylene oxide in the presence of selectivity-enhancing metalate anion which is in association with electropositive complexing sites on a solid support. Often, the electropositive complexing sites contain hydrocarbyl moieties and are thus encompassed within the group of organometalates. Because the metalate anion is in association with a complexing site on a solid, the recovery of metalate anion from glycol product can be effected by phase separation. Readily available solids include anion exchange resins.

The use of metalate anion-containing materials that are in association with some types of organic-containing cations, such as anion exchange resins, deserves further comment in that they are subject to degradation and lose metalate anion content. Copending U.S. patent application Ser. No. 594,267, filed on even date herewith, of B. T. Keen, et al., is directed to processes for enhancing the stability of metalate anion-containing material by adding small amounts of a more water-soluble metalate anion-containing material.

The five foregoing described patent applications U.S. Ser. Nos. 428,815; 530,235 594,385; 594,256; and 594,268 are hereby incorporated by reference.

In order to provide a commercially-attractive process for making alkylene glycols in the presence of selectivity-enhancing metalate anion, it is thought to be necessary that the process be operable on a continuous basis. Further, the metalate anion should be recoverable in a form suitable for reuse in the hydrolysis reaction for purposes of economy. The alkylene glycol product should also be sufficiently free of the metalate anion that it provides commercially-desirable products such as polyester grade ethylene glycol.

However, difficulties have been noted in recovering metalate anion from alkylene glycol product. In particular, the metalate anion is subject to degradation, e.g., by reduction, thereby rendering the metalate anion unsuitable for reuse.

Japanese Kokai No. 56/92228, published July 25, 1981, and Kokai No. 56/118024, published Sept. 16, 1981, disclose processes for producing highly pure alkylene glycols. Kokai No. 56/92228 discloses a process in which alkylene oxide, water and gaseous carbon dioxide are reacted in the presence of a catalyst containing molybdenum and/or tungsten (potassium molybdate was exemplified). An additive such as compounds of alkali metals, compounds of alkaline earth metals, quaternary ammonium salts and quaternary phosphonium salts (potassium iodide is specifically exemplified) may be employed. Carbon dioxide is stripped from the alkylene glycol containing liquid, and then alkylene glycols are stripped to provide a bottom residue containing the catalyst. According to the disclosure, it is essential that the water content of the bottom residue be maintained at a concentration of at least 0.1 weight percent, preferably at least 1 weight percent, particularly 1 to 100 weight percent based on the catalyst. It is noted that if the bottom residue has a water content of less than 0.1 weight percent based on the catalyst and is recycled to the reactor, the yield of monoalkylene glycol is reduced. In the final step, the overhead from the previous stripping zone is distilled to separate water from the alkylene glycol product.

The disclosure of Kokai No. 56/118024 is somewhat similar in that a stripping operation is used to recover the catalyst and the bottoms residue must contain water. The process differs in that no carbon dioxide or additive is necessarily employed in the reaction zone, but the pH of the reactor is at a pH of 5 to 10, and the carbon dioxide stripping step is not conducted.

Not only is the effectiveness of the catalyst potentially adversely affected if sufficient water is not present in the bottoms residue according to these Kokais, but, also, a portion of the alkylene glycol becomes oxidized and off-color and is of poor quality.

Although the Kokais represent that the processes can provide highly pure alkylene glycols, certain disadvantages exist such as the need to carefully monitor the amount of water in the bottoms residue to assure that poor quality alkylene glycol is not produced. More significantly, the processes are energy intensive in that the alkylene glycol product and water (since it is lower boiling than alkylene glycols) must be removed as the vapor phase from the catalyst-containing bottoms. Moreover, the temperatures required to accomplish this separation at feasible vacuum conditions exacerbate the risk of degradation of the catalyst.

OVERVIEW OF THE INVENTION

The processes of this invention can enable the recovery of selectivity-enhancing metalate anion that was present during the hydrolysis of alkylene oxide to alkylene glycols. Moreover, the alkylene glycol product can be of desirable quality for commercial processes. Further, the processes enable the recovery of the metalate anion in an attractive, integrated manner, particularly from an energy standpoint.

In accordance with the processes of this invention, alkylene oxide and water are provided to a hydrolysis zone containing selectivity-enhancing amounts of metalate anion. The hydrolysis zone is maintained under conditions sufficient to form an aqueous solution of alkylene glycol wherein the aqueous solution also contains metalate anion. An alkylene glycol-containing stream is withdrawn from the hydrolysis zone that contains metalate anion and is contacted with a solid having electropositive complexing sites thereon which are in association with a replaceable anion wherein the electropositive complexing sites have a greater affinity for the metalate anion than the replaceable anion. The contacting is under conditions such that the content of the metalate anion in the alkylene glycol-containing stream is reduced. Because of their ready availability, particularly attractive solids that are useful in processes of this invention are anion exchange resins.

Since the processes of this invention recover metalate anion from alkylene glycol-containing streams by association with electropositive complexing sites on a solid, the energy required for the separation is relatively small. Moreover, the metalate anion need not be subjected to conditions that promote degradation of the anion and/or result in discoloration or other deterioration of the alkylene glycol product.

Advantageously, in accordance with an aspect of the invention, the solid, after recovering metalate anion, is used as the metalate anion source for further hydrolysis of alkylene oxide. Hence, the processes can be integrated so as to provide a commercially attractive operation both from the standpoints of recovering and reusing metalate anion and the relatively small energy requirements.

THE METALATE ANION RECOVERY

In the processes of this invention, the metalate anion is recovered from an alkylene glycol-containing stream by contact with a support having electropositive complexing sites associated with a replaceable anion. The conditions of the contacting are such that the metalate anion exchanges with the replaceable anion and thereby becomes associated with the solid phase.

In order for this exchange to occur the electropositive complexing sites have a greater affinity for the metalate anion than the replaceable anion. There are several factors that affect the affinity of an electropositive complexing site to a particular anion as opposed to another anion. The first is the intrinsic affinity, i.e., the strength of association between the electropositive complexing site and the anion. While it is preferable that the metalate anion have a greater intrinsic affinity toward the electropositive complexing sites, it is not essential to provide operable processes in accordance with this invention. A second factor takes into account the equilibrium nature of the exchange. The relative concentrations of the metalate anion and the replaceable anion in the environment of the electropositive complexing site will play a role.

The replaceable anions are those that are capable of being exchanged for the metalate anion. When the quality of the alkylene glycol is important, the replaceable anion should not unduly adversely affect the product quality or should be capable of being removed from the alkylene glycol to the extent necessary to provide an advantageous product. The replaceable anion should therefore exhibit good stability in the presence of water and alkylene glycol, particularly at elevated temperatures, so that the problems characteristic of metalate anions such as discoloration of the alkylene glycol product do not occur. It is also possible in some instances to treat the alkylene glycol after contact with the electropositive complexing sites to render the replaceable anion into an innocuous form. For example, if the replaced anion is hydroxide, the alkylene glycol-containing stream may be treated with an acid to yield water.

Various anions may find application as replacement anions including hydroxyl; mineral anions such as the halides (e.g., chloride, iodide, bromide), oxyanions such as sulfate, sulfite, phosphate, phosphite, borate, nitrate, nitrite, and carbonate and organic anions such as acetate, propionate, and oxalate; and the like. Because of availability, anions such as hydroxyl, chloride and iodide are most often used, and hydroxyl is most preferred. However, not all replaceable cations will be suitable in all instances. Considerations such as the effect on the stability of the solid or electropositive complexing sites exist as well as the relative affinity as compared to metalate anion in respect to the electropositive complexing sites. Moreover, since an equilibrium relationship exists, the replaceable anion should preferably be one which is substantially absent from the alkylene glycol-containing stream passed to the solid having the electropositive complexing sites thereby favoring the exchange.

The electropositive complexing sites for association with metalate are on a water-insoluble support which may be organic or inorganic, i.e., the support is solid under the processing conditions. The electropositive complexing sites and the water-insoluble support are substantially non-reactive with water, alkylene oxide and alkylene glycol. The preferred electropositive complexing sites and the solid supports are those whose degradation products do not adversely affect the quality of alkylene glycol or can facilely be removed from the alkylene glycol product. Typical electropositive complexing moieties can contain strongly electropositive complexing groups such as quaternary ammonium groups, quaternary phosphonium groups, fulfonium groups, or arsonium groups or moderately electropositive complexing groups such as protonated tertiary amines and protonated tertiary phosphines. Because of the stability and availability of quaternary ammonium and tertiary amine groups, they are generally preferred. Suitable electropositive complexing groups include those having the general formula:

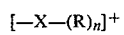

wherein X is nitrogen, phosphorous, sulfur, or arsenic bonded directly or indirectly to the support; and R may be the same or different and is hydrogen, monocyclic aryl or aralkyl of 6 to 8 carbon atoms, monocyclic alkaryl of 7 to 9 carbon atoms, or alkyl or alkoxy of 1 to about 6 carbon atoms, and R may be substituted with groups which are substantially non-reactive with alkylene oxide, alkylene glycol, or water, e.g., hydroxy groups such as hydroxyalkyl substituents, haloalkyl substituents, silyl substituents, siloxy substituents, and the like; and n designates that sufficient R groups are provided to satisfy the remaining valencies of X, e.g., n is 3 and X is nitrogen when the electropositive complexing site is a quaternary ammonium. Frequently, the stability of the electropositive complexing sites is enhanced when R is lower alkyl, especially methyl. It is also possible for X to be contained in a heterocyclic structure. Frequently, such cyclic structures contain 5 or 6 ring members with one or two members being the charge-carrying center X.

The electropositive complexing site may be bonded to the solid support through, for example, an alkylene, arylene, silyl or siloxy group.

Solid supports having electropositive complexing sites include inorganic substrates, such as carbon, silica gel, zeolite, clay and glass beads. These supports may have the electropositive complexing sites affixed through adsorption, reaction or graft polymerization. See, for instance, Japanese Kokai Nos. 50/32085 and 52/26386. See also, P. Tundo, et al., "Anion-Exchange Properties of Ammonium Salts Immobilized on Silica Gel," *J. Am Chem. Soc.*, Vol. 104, pp 6547–6551 (1982), and P. Tundo, et al., "Phase-Transfer Catalysts Immobilized and Adsorbed on Alumina and Silica Gel", *J. Am. Chem. Soc.*, Vol 104, pp 6551–6555 (1982). U.S. Pat. No. 4,430,496 discloses silyl alkylammonium sites on inert particles. See also German patent application No. 2,433,409. The above are all hereby incorporated by reference.

Suitable supports for the electropositive complexing sites also include water-insoluble anionic resins. The resin can be varied to convenience and can comprise essentially any resinous composition. The resins include high molecular weight polymers and copolymers, e.g., addition and condensation polymers, including polyalkylene, polyesters, polycarbonate, polysulfones, polyimides, phenolic resins, formaldehyde resins, polyurethanes, and the like, and the electropositive complexing sites may be adsorbed, reacted or grafted on the resin. While many available resins are carbon-based, silica-based resins may also find application in processes in accordance with this invention. These resins include organosiloxane polymers, such as dimethyl polysiloxane, methylphenyl polysiloxane, methyl vinyl polysiloxane, cyanoalkylmethyl polysiloxanes and fluoroalkylmethyl polysiloxanes. See, for example, U.S. Pat. No. 4,417,066, issued Nov. 22, 1983, pertaining to organosiloxane polymers containing quaternary ammonium sites. U.S. Pat. No. 4,410,669 discloses polymeric ammonium compounds with a silica-type backbone which are said to exhibit good thermal stability and inertness to chemical attack. Both of these patents are herein incorporated by reference.

Monomers which can be employed in preparing carbon-based resins include styrene and styrene derivatives such as methylstyrene, ethylstyrene, vinylnaphthalene, 3,4,6-trimethylstyrene, chlorostyrene, methoxystyrene, N,N-dimethylaminostyrene, nitrostyrene, chlorostyrene, trifluorostyrene, trifluoromethylstyrene and aminostyrene; butadiene; acrylonitrile and acrylonitrile derivatives; acrylic acid and acrylates such as methyl acrylate and chloromethyl acrylate; methacrylic acid and methacrylates such as cyclohexyl methacrylate, dimethylaminoethyl methacrylate, glycidyl methacrylate and methyl methacrylate; maleates such as diethyl maleate; fumarates such diethyl fumarate; vinyl ketones such as methyl vinyl ketone and ethyl isopropyl ketone; vinylidenes; acrylamide and acrylamide derivatives; aliphatic acid vinyl esters such as vinyl acetate, vinyl butylate and vinyl caproate; formaldehyde with, e.g., phenol, xylene, urea, melamine; bisphenol A; sulfones such as dichlorodiphenyl sulfone; phosgene; toluene diisocyanate; polyols such as ethylene glycol; epoxybutadiene; etc.

For purposes of strength and chemical resistance, the resin is preferably cross-linked. Representative resins which can be cross-linked include styrene-divinylbenzene, styrene-glycol dimethacrylate, aniline-formaldehyde, aryl polyamine-formaldehyde, phenol-formaldehyde, polyacrylate, and the like. Generally, the amount of cross-linking agent provided is an amount of about 4 or 5 to 30 or 40 mole percent based on the monomer used to prepare the resin.

Cross-linking agents which can be employed in preparing resins include divinylbenzene, divinyltoluene, divinylnaphthalene, divinylethylbenzene, trivinylbenzene, divinyldiphenylmethane, divinylbenzyl, divinylsulfone, divinylketone, bis(vinylpyridinoethyl)ethylene diamine, diallyl phthalate, triallylamine, N,N'-ethylenediacrylamide, ethylene glycol dimethacrylate, triethylene glycol dimethacrylate, trimethylolpropane trimethacrylate, trimethylolpropane triacrylate, triallyl isocyanurate and diallyl melamine.

The resins can take many forms, such as swellable gels, semi-porous or iso-porous resins, or macro-porous (macro-reticular) resins. The resins may be spherical or irregular granules which in turn may be supported on a larger solid structure. Frequently, the major dimension of the resins is about 0.1 to 5 millimeters (e.g., 0.3 to 1 or 2 millimeters).

Anion exchange resins having quaternary amine sites and tertiary amine sites are commercially available. These resins include resins with acrylic matrices such as Amberlite ™ IRA-68, IRA-60, and XE-258 resins available from Rohm & Haas Co.; phenolic-containing matrices such as Amberlite ™ IRA-4B resin available from Rohm & Haas Co.; styrene-divinylbenzene matrices such as Amberlite ™, IRA-900, IRA-904, IRA-93, IRA-94, and IRA-400 resins available from Rohm & Haas Co., Dowex ™ 1, 2, 11, WGR, MSA-1, and MWA-1 resins available from the Dow Chemical Company, and Duolite ™ A-101, A-102, and A-114, available from the Diamond Shamrock Corp.

Preferably, the support has at least about 0.1, e.g., 0.5 to 10, say 0.5 to 5 milli-equivalents of exchange capacity (based on the pendant electropositive complexing sites) per gram of dry support. It is at these sites that the association occurs between the metalate anion and the insoluble support.

The contacting of the alkylene glycol-containing stream with the electropositive complexing sites is under conditions such that the metalate anion content of the alkylene glycol-containing stream is reduced. The amount of reduction of metalate anion will depend upon, among other things, the intrinsic affinity of the metalate anion and replaceable anion to the electropositive complexing sites, the relative concentrations of the metalate anion and the replaceable anion in the environment of the electropositive complexing site, the degree of dispersion of the alkylene glycol-containing stream throughout the bed of the solid having the electropositive complexing sites, the amount of metalate anion sought to be removed and the amount of solid containing the electropositive complexing sites present.

Typically, at least about 50, often, at least about 75, and sometimes between about 90 and 95 or 99, mole percent of the metalate anion is removed. The processes in accordance with this invention are most attractive when the alkylene glycol-containing stream has relatively little metalate anion, e.g., less than about one percent by weight. Thus, this invention is particularly advantageous in cases in which the hydrolysis is conducted in the presence of metalate anion associated with electropositive complexing sites or a support such as disclosed in the above mentioned U.S. patent application Ser. No. 594,268 including processes in which a small amount of metalate anion-containing material is added to the hydrolysis menstruum to enhance the stability of the support having the electropositive complexing sites such as disclosed in U.S. patent application Ser. No. 594,267, filed on even date herewith, of B. T. Keen, herein incorporated by reference. Hence, the concentration of metalate anion in the alkylene glycol-containing stream passed to the electropositive sites for removal of metalate anion can be less than 1000 ppm by weight, e.g., about 20 to 1000, say, about 5 to 250, ppm by weight.

The amount of electropositive complexing sites provided is primarily dependent upon the intended service life before regeneration or replacement, particularly in continuous processes. Usually, the mole ratio of electropositive complexing sites to the desired amount of metalate to be removed is in the range of about 100:1 to 1:1, e.g., about 10:1 to 1.05:1.

The temperature and pressure conditions of the contacting between the alkylene glycol-containing stream and the electropositive complexing sites for the removal of metalate anion preferably do not unduly adversely affect the metalate anion, the alkylene glycol and/or the support containing the electropositive complexing sites. Advantageously, the conditions are suitable for integration into a hydrolysis process and, therefore, the conditions of temperature and pressure may approximate, or be substantially the same as, those employed for the hydrolysis. Temperatures lower than those used in the hydrolysis process may also be used. Thus, the temperature is frequently between about 0° to 250° C., say, about 20° C. to 200° C. With heat sensitive materials, temperatures within the range of about 20° to 150° C., say, about 20° to 120° C. or 130° C., may be employed. The pressure may be subatmospheric, atmospheric or superatmospheric, e.g., from about 10 millibars absolute to 1000 or more bars absolute, but is generally above atmospheric for convenience, e.g., between about 0.1 and 1000 kilograms per square centimeter gauge.

The alkylene glycol-containing stream may be directly obtained from the hydrolysis or may be processed by, e.g., heat exchange, evaporation, distillation, filtration, adsorption, extraction (such as described in U.S. patent application Ser. No. 594,266, filed on even date herewith, of B. T. Keen, et al., to remove organometalates, i.e., materials having an organic-containing cation and a metalate anion, from alkylene glycol-containing streams), and the like. U.S. patent application Ser. No. 594,266 is herein incorporated by reference.

The support having the electropositive complexing sites, after contact with the alkylene glycol-containing stream, may be regenerated, e.g., by contact with an aqueous solution of a dissolved salt of the replacement ion. Alternatively, the support containing the electropositive complexing sites may be used for the purpose of providing metalate anion for enhancing the selectivity of the hydrolysis either directly or with further exchange with metalate anion.

The association of the metalate or replacement anion with the electropositive complexing sites on the support may be effected in any convenient manner. Usually the placing of the anion on the support is accomplished by a loading technique whereby a soluble salt is contacted in solution in an inert liquid medium with the insoluble support to displace original anion at the site. The counter ions to the anions are preferably water soluble and include alkali metals, alkaline earth metals, ammonium ion, copper, zinc, iron, quaternary ammonium cations, quaternary phosphonium cations, sulfonium cations, and other cations. Inert liquid media include water, aliphatic and aromatic hydrocarbons and substituted hydrocarbons such as hexane, benzene, toluene, xylene, o-dichlorobenzene, methylene chloride, chloroform, carbon tetrachloride, and the like.

The loading can occur at any temperature at which the anion-containing salt is dissolved. The temperature employed is preferably below that which results in unduly adverse effects. Usually, the temperature will be about 0° C. to 120° C., say, about 15° C. to 100° C. Any convenient pressure may be employed, and subatmospheric pressures may assist in the dispersion of the anion throughout the support. The loading process is typically conducted under a suitable atmosphere which frequently may be a substantially inert atmosphere, such as air or nitrogen, for a sufficient period of time to enable desired amounts of anion to become associated with the electropositive complexing sites. This period of time will generally vary with the method, reagents and conditions employed, but it will often be about 0.5 to 50, say about 1 to 15 hours. The resulting product containing the desired anion may be recovered by any convenient physical separation technique, such as filtering, decanting and evaporating.

In order to obtain the desired metalate in association with the electropositive complexing sites on the insoluble support, it is not necessary to use the metalate form. Indeed, any form of the metal which will yield the metalate by reaction subsequent to the loading, including in situ during the hydrolysis reaction, is believed to be suitable. The metal-containing anions may therefore contain halide, e.g., chloride and iodide; sulfide, aliphatic or aromatic hydrocarbon, or similar substituents. The selection of the metalate or precursor of the metalate will, in general, be dependent upon the availability of the compound and its processing characteristics in order to form the association with the electropositive complexing sites of the insoluble support and, in the case of the precursors to the metalate, additionally the ability to form the desired product.

Typically during loading, the mole ratio of anion to the electropositive complexing sites is between about 1:100 to about 100:1, and frequently is between about 1:1 to 25:1. In the prepared product with the associated anion, the ratio of electropositive complexing sites having associated anion to total electropositive complexing sites is frequently between about 1:10 to 1:1, preferably about 0.9:1 to 1:1. It has generally been noted that even though a metalate anion may have a negative charge of two or more, such as molybdate and tungstate, the metalate anion may be associated with only one electropositive complexing site. Typically, the metalate loaded support comprises, as determined by conventional elemental analysis, at least about 0.1, and preferably at least about 1, say, 2 to about 30, e.g., about 5 to 25, weight percent of the metal of the metalate (metal basis) based on total weight of the dry support. The saturation of the electropositive complexing sites of the insoluble support is the only limitation upon the maximum weight percent of metalate contained in association with the electropositive complexing sites on the insoluble support. It is generally desired to achieve as close to saturation levels as possible for reasons of activity and life.

THE HYDROLYSIS PROCESS

Alkylene oxides which may be used to produce alkylene glycols in the processes of this invention are vicinal alkylene oxides having the general formula:

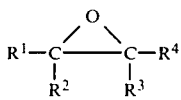

wherein $R^1$, $R^2$, $R^3$ and $R^4$ are the same or different and are hydrogen or hydrocarbyl-containing substituents of 1 to about 20 carbon atoms. Often $R^1$, $R^2$, $R^3$ and $R^4$ are hydrogen, alkyl of between 1 and about 10 carbons, monocyclic or bicyclic aryl having up to about 12 carbons, alkaryl having 7 to about 10 carbons, monocyclic or bicyclic aralkyl having 7 to about 15 carbons, alkenyl having 2 to 3 carbons, cycloalkyl having 3 to about 8 carbons, and cyclic structures joining two of $R^1$, $R^2$, $R^3$ and $R^4$ having 3 to about 8 carbon atoms. Representative of alkylene oxides are ethylene oxide, propylene oxide, butylene oxide, including isobutylene oxide, 1,2-butylene oxide and 2,3-butylene oxide, pentylene oxide, styrene oxide, cyclohexene oxide and the like. Preferably, the alkylene oxide is an aliphatic alkylene oxide having 2 or 3 carbon atoms, i.e., ethylene oxide and propylene oxide.

Alkylene oxides are well known, as is their preparation. For example, alkylene oxide can be prepared by reacting an olefin with an organo-hydroperoxide in the presence of a catalyst or by the partial oxidation of an alkene with a molecular oxygen-containing gas in the presence of a silver catalyst.

Water (as the liquid or steam) is also employed as a reagent for the formation of the corresponding alkylene glycol. Usually the water is of sufficient purity to provide a suitable quality alkylene glycol product. Liquid water may be distilled or demineralized, for example, by ion exchange treatment.

The metalate anions are characterized by an anionic structure containing at least one metal atom and at least one oxygen ligand which is conventionally characterized as a double-bonded oxygen atom.

The metalate anions which may be useful in the processes of this invention comprise a polyvalent metal having a positive functional oxidation state, often an oxidation state of at least +3, say, +4 to +6, and may be a transition metal. The metalate anions may be illustrated by the following formula:

$$[(A)_q M(O)]^{a-}$$

wherein a— is the negative charge of the anion, which is usually between —1 and —4, A is one or more substituents to fill the remaining valencies (q) of M and may be the same or different and may be, for instance, double-bonded oxygen; an organic radical such as an alkyl, alkoxy, acyl, aryl, amino, phosphine, etc., usually of 1 to about 12 carbon atoms; halogen (e.g., chlorine, fluorine, iodine); —O— or —S— wherein the remaining valency of the oxygen atom is in free ionic form or is bonded to a metal atom (as in a bimetal or polymetal-containing metalate) or cation. Most commonly A is —O— or =O. Even when the A in the starting organometalate is other than —O—, e.g., chlorine, it is possible that the original substituent becomes replaced by —O— in the course of the process.

Particularly preferred metals for the metalate anions include the metals in groups Vb and VIb of the periodic chart such as vanadium, molybdenum and tungsten, although other metals such as rhenium and germanium may also find application. Representative metalate anions which are especially useful include molybdate, tungstate, metavanadate, hydrogen pyrovanadate and pyrovanadate; although because of the complex chemistry associated with many metalate anions, the precise structure of the operative specie or species may be different. Frequently the metalate anion is an anion conventionally characterized by a formula such as $[MoO_4]^{2-}$, $[VO_3]^-$, $[V_2O_7H]^{3-}$, $[V_2O_7]^{4-}$, and $[WO_4]^{2-}$; however, it is recognized that the chemistry of these metalate anions, particularly the vanadates, is complex, and the exact chemical formula under the conditions of the process may prove to be different.

Not all metalate anions, including those of vanadium, tungsten and molybdenum, exhibit desired activity with alkylene oxide. For example, it has been observed that paramolybdate and paratungstate anions (as the added metalate anion) appear to exhibit less, if any, activity for enhancing selectivity.

Advantageously, the metal for the metalate anion is selected on the basis of the nucleophilicity and electrophilicity in the anion with respect to alkylene oxide in the environment. For example, the metal as in the metalate often has a nucleophilicity with respect to ethylene oxide greater than that exhibited by rhenium as rhenate anion under the same conditions. Also, it is frequently the case that the metal as the metalate has an electrophilicity with respect to ethylene oxide greater than that exhibited by vanadium as orthovanadate (as that species) under the same conditions.

A particularly convenient method for approximating nucleophilicity and electrophilicity characteristics of a metal in a metalate anion is by comparing the rate and selectivity to monoethylene glycol under substantially the same hydrolysis conditions but employing an equimolar amount (based on the anion) of the subject metalate anion and the reference anion. For the sake of ease, the cation may be sodium. If the rate and/or selectivity to the monoethylene glycol is less than that provided by the rhenate anion, then the metal as the metalate is probably less nucleophilic than rhenate with respect to ethylene oxide. If the production of diethylene glycol and polyethylene glycol is greater than that provided with orthovanadate, regardless of the rate of formation of glycols, then the metal as the metalate is probably less electrophilic than orthovanadate with respect to ethylene oxide.

The metalate anions are associated with a cation and are dissociatable from the cation. Although the cations may be substantially insoluble, or have little solubility, in water at reaction conditions, the metalate anion can provide the enhanced selectivity to monoalkylene glycol. However, if the metalate anion is too tightly bound, it will not have the desired activity. Thus, calcium vanadate, which has little solubility in water and retains the metalate anion tightly bound, has not been found to be an acceptable metalate-containing compound. On the other hand, where the cation is, for instance, an essentially insoluble quaternary ammonium moiety, the dissociatable nature of the metalate anion is believed to permit its usefulness to achieve enhanced selectivities to monoalkylene glycol.

Particularly advantageous metalate anion-containing materials for use in the hydrolysis menstruum to enhance selectivity to monoalkylene glycol are those having metalate anion in association with electropositive complexing sites on solid support such as discussed in U.S. patent application Ser. No. 594,268. Suitable supports containing electropositive complexing sites include those described above in connection with the electropositive complexing sites on support used to remove metalate anion except that the anion is the metalate anion.

Other metalate anion-containing materials may be represented by the formula:

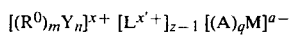
  I.

wherein $[(R^0)_m Y_n]^{x+}$ is an organic-containing cation having a positive charge of x and Y is a polyvalent element, which is an ionic charge carrying center, $R^0$ is hydrogen or hydrocarbyl-containing substituent with the proviso that the organic-containing cation has at least one $R^0$ which contains a hydrocarbyl substituent, m is the average number of electron pairs shared by Y with the total $R^0$ groups, n is the number of charge carrying centers, wherein m, n and x are related by the equation $x = n(V-m)$ in which V is the average functional oxidation state of Y wherein each electron pair used by each Y in bonding to $R^0$ is given the value of 1 and the functional oxidation state of Y is the sum of the electron pairs bonding to $R^0$ and x/n, wherein x is an integer of 1 or 2; wherein L is a cation which has a positive charge of x' and which may be the same or different from the organic-containing cation, where x' is usually 1 or 2; wherein z is the number of organic-containing cations which is from 1 to 3. Hence, the metalate anion having a negative charge, a, of the metalate anion equals the amount of $x + [(z-1)(x')]$.

The hydrocarbyl-containing substituents useful in the organic-containing cation frequently contain at least four carbon atoms, and may be further substituted with moieties that are not reactive with the anion.

L may be any suitable cation and often is another organic-containing cation or a non-organic-containing cation which serves to balance the charge of the anion. L may include alkali metals, alkaline earth metals, copper, zinc, iron, ammonium cations, phosphonium cations, sulfonium cations, and other cations including organic-containing cations, e.g., containing alkyl, alkoxy, acyl, aryl, amino, phosphino, etc., groups of 1 to about 12 carbons.

Suitable cations may include structures represented by the formulae:

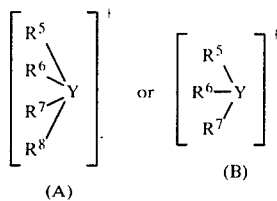

where Y is nitrogen, phosphorous, or arsenic for formula A, or sulfur for formula B, i.e., ammoniums, phosphoniums, arsoniums and sulfoniums, where each of $R^5$, $R^6$, $R^7$ and $R^8$ may be the same or different and may combine to form cyclic structures. Exemplary of each of $R^5$, $R^6$, $R^7$ and $R^8$ are hydrogen and unsubstituted and substituted hydrocarbyls of 1 or more carbon atoms, e.g., to about 70 carbon atoms. Representative cations are disclosed in copending U.S. patent application Ser. No. 594,264, filed on on even date herewith, of J. R. Briggs and J. H. Robson, herein incorporated by reference.

Other organic-containing cations which may be useful include the bis(hydrocarbyl-phosphine) iminiums represented by the formula

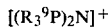

wherein each $R^9$ may be the same or different and may be the same as set forth for $R^5$ to $R^8$. Illustrative iminiums are disclosed in Ser. No. 594,264.

Illustrative of the organic-containing cations are tetrahydrocarbyl ammoniums, e.g., tetramethyl ammonium, tetraethyl ammonium, tetra-n-propyl ammonium, tetra-n-butyl ammonium, tetra-isobutyl ammonium, trimethyl butyl ammonium, tetraheptyl ammonium, tetraphenyl ammonium, tetrabenzyl ammonium, tetradodecyl ammonium, tetraoctadecyl ammonium, and the like; trihydrocarbyl ammonium, e.g., trimethyl ammonium, triethyl ammonium, triphenyl ammonium, tridodecyl ammonium, trioctadecyl ammonium, and the like; dihydrocarbyl ammoniums, e.g., dimethyl ammonium, diethyl ammonium, di-n-butyl ammonium, di-n-heptyl ammonium, diphenyl ammonium, dibenzyl ammonium, didodecyl ammonium, dioctadecyl ammonium, and the like; hydrocarbyl ammoniums, e.g., methyl ammonium, n-butyl ammonium, dodecyl ammonium, octadecyl ammonium, phenyl ammonium, benzyl ammonium, and the like; tetrahydrocarbyl phosphoniums, e.g., tetramethyl phosphonium, tetraethyl phosphonium, tetra-n-propyl phosphonium, tetra-n-butyl phosphonium, tetra-isobutyl phosphonium, trimethyl butyl phosphonium, tetraheptyl phosphonium, tetraphenyl phosphonium, tetrabenzyl phosphonium, tetradodecyl phosphonium, tetraoctadecyl phosphonium, and the like; trihydrocarbyl phosphonium, e.g., trimethyl phosphonium, triethyl phosphonium, triphenyl phosphonium, tridodecyl phosphonium, trioctadecyl phosphonium, and the like; dihydrocarbyl phosphoniums, e.g., dimethyl phosphonium, diethyl phosphonium, di-n-butyl phosphonium, di-n-heptyl phosphonium, diphenyl phosphonium, dibenzyl phosphonium, didodecyl phosphonium, dioctadecyl phosphonium, and the like; hydrocarbyl phosphoniums, e.g., methyl phosphonium, n-butyl phosphonium, dodecyl phosphonium, octadecyl phosphonium; phenyl phosphonium, benzyl phosphonium, and the like; bis(hydrocarbyl-phosphine)iminiums such as bis(triphenyl-phosphine)iminium, bis(tribenzyl-phosphine)iminium, bis(trimethylphosphine)iminium, bis(tridodecyl-phosphine)iminium, and the like; quaternized diamines such as N,N'-bis(trimethyl)propylene diamine, N,N'-bis(triphenyl)propylene diamine, N,N'-bis(trioctadecyl)propylene diamine; and quaternized diphosphines such as P,P'-bis(trimethyl)propylene diphosphine, and the like.

The metalate anion may be provided to the reaction mixture as a metalate anion or in a form which is converted to the desired metalate anion by subsequent chemical reaction. Hence, halide, sulfide, or the like, metal-containing compounds may be employed as the precursor to the desired metalate anion. Some of these precursor compounds may be converted to metalates during the hydrolysis reaction.

In general, the hydrolysis reaction involves providing alkylene oxide, water and organometalate to a reaction zone. The relative amounts of these components and the presence of one or more solvents or adjuvants can vary widely depending upon the sought selectivity to monoalkylene glycol, the sought hydrolysis ratio, and the type of hydrolysis reaction system used. Hence, the optimal operating parameters will vary. However, the general considerations for the processes will be common to many of the hydrolysis reaction systems. The following discussion provides a guide to conditions which are often encountered in the processes of this invention.

Usually, the amount of the aqueous phase is selected in respect to the amount of alkylene oxide employed in the process since it is a reactant and must be separated from the alkylene glycol products. The unreacted water serves as a heat sink to assist in maintaining desired temperatures during the exothermic hydrolysis reaction. Its importance, however, can vary. With homogeneous processes, it can be a significant consideration. When employing a two-phase process, the solvent present also serves as a heat sink and will therefore reduce the need for water as a heat sink. In two-step processes, the interaction between the alkylene oxide and metalate forms an associated moiety. (For all purposes herein, the associated moiety will be encompassed within the term alkylene oxide.) When this associated moiety is contacted with water, alkylene glycol is produced but the heat produced is considerably less than that produced by the reaction of alkylene oxide with water. Consequently, in the two-step processes, the role of water as a heat sink may be relatively minor.

The mole ratio of water (which under the conditions of the process may be provided in liquid form or steam) to alkylene oxide is often in the range of about 0.5:1 to 50:1, and preferably, the amount of water employed is at least sufficient on a stoichiometric basis to react with all the alkylene oxide provided, e.g., the mole ratio is at least 1:1 up to, say, about 40:1 or 50:1, say, about 1:1 to 20:1.

It is believed that the hydrolysis reaction in the processes of this invention can proceed by at least two routes, one involving the selectivity-enhancing metalate and the other being the conventional route. Thus, the processes of this invention are capable of producing dialkylene glycol and higher glycols. Hence, the lower the ratio of water to alkylene glycol, all other factors remaining the same, the greater the amount of these dialkylene and higher glycols that will be produced. This provides a degree of flexibility in operating processes of the invention to provide a desired amount of these higher glycols but an amount less than would be obtained in a conventional process. In most instances, this mole ratio is in the range of about 3:1 to 10:1; however, for two-step processes, lower mole ratios are frequently preferred, say, about 1:1 to 5:1.

Another factor affecting the degree of selectivity to the monoalkylene glycol is the amount of metalate anion employed. Generally, the greater the amount of metalate anion employed, the higher the selectivity to monoalkylene glycol, all other factors remaining the same. Thus, the mole ratio of metalate anion to alkylene oxide may be up to 5:1 or 10:1 or more. Economics usually dictate that the mole ratio of metalate anion to alkylene oxide will be less than about 2:1. Often, the mole ratio is at least about 0.001:100, say, in the range of about 0.05:100 to 2:1, e.g., about 0.1:100 to 1:1, and most frequently about 1:100 to 0.5:1. In two-stage processes, mole ratios of metalate anion to alkylene oxide are often closer to those required for complete association of the alkylene oxide with the metalate anion in order to ensure substantially 100 percent selectivity to the monoalkylene glycol. In processes in which the organometalate is dissolved in the aqueous phase, less organometalate may be required to achieve a given selectivity to monoalkylene glycol than that required to obtain the same selectivity when organometalate is in a separate phase such as in the two-phase processes.

Preferably a solid which contains metalate anion in association therewith is used in the reaction zone. When using such solids, the availability of metalate anions sites to alkylene oxide may be hindered by the solid structure. Thus, greater ratios of metalate anion to alkylene oxide are preferred, say, about 0.01:1 to 20:1, e.g., about 0.05:1 to 15:1.

For purposes of determining the moles of metalate anion present, in respect to anions containing more than one site which is available for association with alkylene oxide, e.g., molybdate and tungstate, the moles shall be calculated based on the number of such sites.

In hydrolysis reaction processes such as the two-step process and the two-phase process, a substantially water-insoluble solvent is typically present, and the organometalate is dissolved therein.

The amount of solvent, when employed, can vary widely and is frequently in the range of about 0.1:1 to 10:1 volumes per volume of water. The amount of solvent employed is often determined based upon the solubility of the metalate anion-containing material in the solvent, whether the substantially water-insoluble phase is to be the continuous phase, the desired mass for the dissipation of heat from the exothermic reaction, and the like.

It some instances it may be desirable to use interactive solvents such as alkylene carbonate and 1,2-dimethoxyethane. These solvents are often miscible with water and can be used in many hydrolysis reaction processes and seem to enhance the selectivity to monoalkylene glycol.

The hydrolysis can be conducted under conditions sufficient to maintain the aqueous phase and the substantially water-insoluble phase and to effect the hydrolysis. The temperature, however, should not be so great that the metalate anion-containing moiety is unduly adversely affected. Frequently, the reaction temperature is between about 20° C. and about 220° C. or 250° C., say, between about 50° C. and 200° C., and sometimes between about 80° C. and 180° C. In some cases, the metalate anion-containing material may be subject to degradation at temperatures in excess of, for example, 140° C. or 150° C., and thus lower temperatures would be advantageous even though the rate of reaction decreases with decreasing temperature.

The processes may be conducted at subatmospheric, atmospheric or superatmospheric pressure. For purposes of convenience, the reaction is typically conducted at pressures greater than ambient, e.g., between about 0.1 and 1000 kilograms per square centimeter gauge, and preferably between about 2 and 100 kilograms per square centimeter gauge.

The hydrolysis may be conducted for a time insufficient for complete reaction, but it is generally preferred that when water is provided in amounts sufficient for complete reaction with the alkylene oxide, the reaction is conducted for a period of time sufficient to ensure that substantially all the metalate anion is reacted. The amount of time required to accomplish the substantially complete reaction is determined by the other conditions employed including temperature, amount of reactants present, and the like. The reaction may be carried out for very short periods of time; e.g., fractions of a second, and, if desired, may be carried out for periods of up to hours, e.g. about 0.01 second to 5 hours, preferably about 1 second to 30 minutes.

The alkylene oxide may be a gas under the conditions of the reaction and may be introduced into the liquid medium as a fine dispersion of gas bubbles, but most frequently, the pressure is sufficient to maintain the alkylene oxide in the liquid phase.

The hydrolysis may be conducted in the presence of a gas, which is preferably inert. Gases which may be employed include air, carbon dioxide, nitrogen, argon and the like. Carbon dioxide is often present by the very nature of the process and the source of the alkylene oxide (especially by partial oxidation of alkenes). Frequently, it is desired to maintain the mole ratio of carbon dioxide to alkylene oxide less than 0.1:1, particularly less than 0.05:1, unless it is desired to affect the pH of the reaction menstruum. Carbon dioxide can be used in certain amounts to enhance the selectivity provided by vanadate anion such as disclosed in U.S. patent application Ser. No. 594,265, filed on even date herewith, of B. T. Keen, herein incorporated by reference.

The pH of the reaction menstruum is frequently maintained relatively neutral, e.g., between about 5 and 11, preferably about 6 to 10.5, and most often the pH is in the range of about 6 to 10. With some metalate anions, such as the vanadates, tungstates and molybdates, the pH of the medium can be determinative of the species present. For example, in strong bases the orthovanadate may predominate, but at neutral conditions metavanadate may exist to the substantial exclusion of the orthovanadate. In another example, more acidic media promote the formation of polynuclear molybdates which often have less, if any, activity towards forming the associated moiety.

The pH may be maintained within the desired range by the addition of acid or base, or the addition of buffers, as is well known in the art. However, the presence and nature of salts should be considered since the cation may displace the cation for the metalate anion. Mechanisms which have been proposed for maintaining the desired pH in other types of hydrolysis processes include the addition of carbon dioxide or inorganic acids or organic acids such as sulfuric acid, hydrochloric acid and acetic acid. The agents for maintaining the pH value of the reaction menstruum may be added in any convenient manner such as during the reaction, e.g., by purging with carbon dioxide, or by addition to one or more of the reactants prior to introducing the reactants into the reactor.

The maintenance of the pH within the desired ranges can also have a secondary effect of enhancing the stability of the metalate anion.

The reaction vessel or vessels for the hydrolysis reaction will differ depending upon the hydrolysis reaction system used. For instance, with a homogeneous system, the apparatus may be a tank or tube having as a primary design criterion providing a sufficient residence time for the reaction. In a two-phase system and some two-step systems, means to provide intimate contact between the aqueous and non-aqueous phases are desirable. Such processes may be conducted in any suitable manner for reactions in menstruum containing more than one phase. For instance, the aqueous phase may provide the continuous phase or the substantially water-insoluble phase may be the continuous phase. In general, it is desired that the discontinuous phase is highly dispersed and is in the form of small bubbles to enhance the interface areas between the phases. For example, the discontinuous phase can have bubble diameters of less than about 2, say, less than about 1, e.g., about 0.01 to 0.5, centimeters. Devices to enhance the dispersion may be employed such as agitators, spargers and the like. The vessels may contain packing, trays and the like to further promote contact. However, in order to obtain an enhanced selectivity to monoalkylene glycol, it is not usually essential to have a dispersed phase. Indeed, the phases may form adjacent layers during conducting the reaction. The feed, or various components, may be pre-mixed before being introduced into the reactor or the components may be separately introduced into the reaction vessel. For instance, a substantially water-insoluble liquid phase can be admixed with alkylene oxide and introduced into an aqueous phase in the reaction vessel. Alternatively, alkylene oxide may be separately introduced into a reaction vessel containing a substantially water-insoluble liquid phase and an aqueous phase. In any event, the process should be operated such that at least a portion of the alkylene oxide has an opportunity to contact the substantially water-insoluble phase containing the metalate anion-containing material prior to reaction with water.

Figure 1:
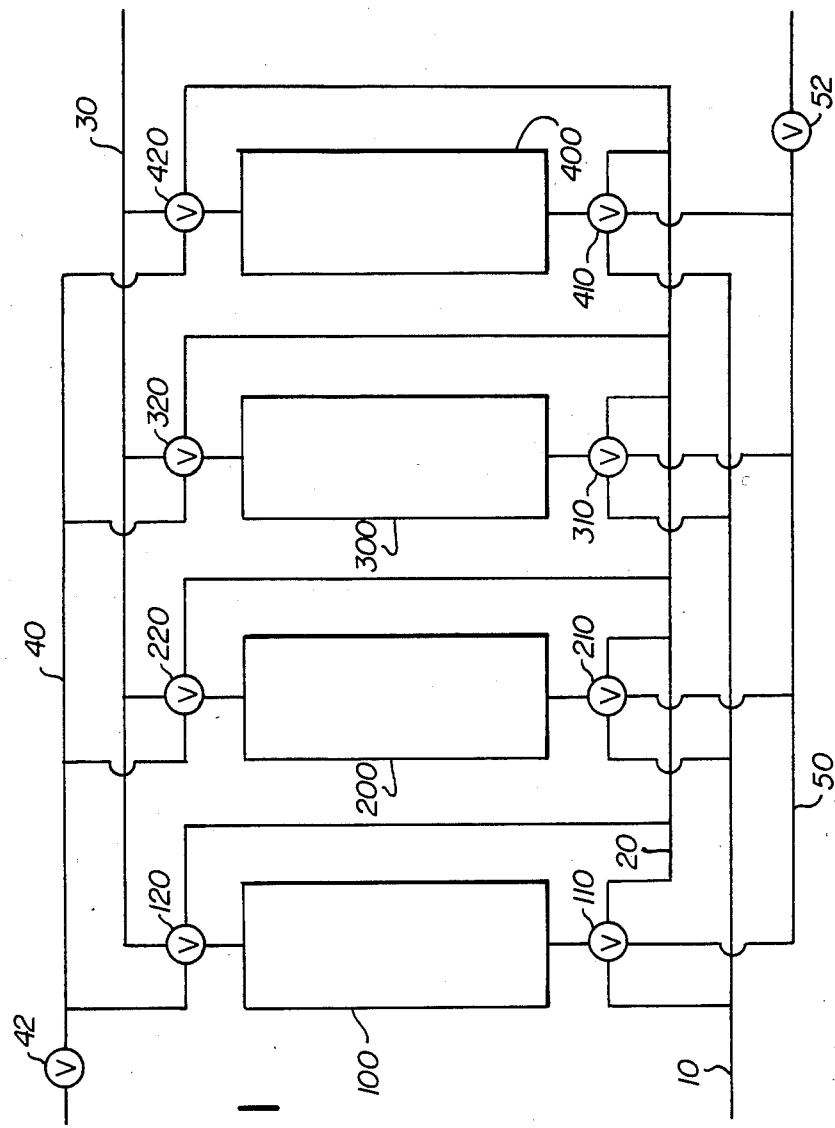
FIG. 1, which is a schematic representation of a process in accordance with this invention, is provided to facilitate the understanding of this invention but is not in limitation thereto. For the sake of simplicity, heat exchangers, pumps, and other such equipment are not depicted.

The system depicted comprises four vessels having beds of, for example, anion exchange resin (vessels 100, 200, 300 and 400) which may be operated in different modes. For example, two vessels may be employed in parallel for conducting the reaction between alkylene oxide and water to form alkylene glycol with the remaining two beds being operated in parallel to remove metalate anion from the alkylene glycol product. Alternatively, two vessels may be used in series for conducting the reaction and two vessels may be used in parallel to recover the metalate anion.

In another mode of operation, one vessel may be off line for recharging, another used for the hydrolysis reaction and the third used to remove metalate anion. The fourth vessel can be contacted with a solution containing metalate anion so that substantially all the electropositive complexing sites are in association with metalate anion. This last mode of operation enables the process to be continuously operated during a change of the anion exchange resin employed. Thus, in following the life of a vessel, a new charge of anion exchange resin that has not been exchanged with metalate anion can be used to remove metalate anion. The rate of recovery of the metalate anion will decrease as the portion of functional sites of the resin that are associated with metalate anion increase. When the rate has dropped so that fresh, unexchanged resin is desired, the vessel can be removed from that operation and then contacted with a solution containing metalate anion to complete the exchange to metalate anion. The vessel can then take the place of another vessel and be used for the hydrolysis of alkylene oxide. The next step in the sequence is to replace the vessel with another for purposes of conducting the hydrolysis reaction. The resin can be discharged from the vessel and replaced with fresh resin (unexchanged) and then used to recover metalate anion.

In instances in which the effluent from the hydrolysis zone contains a cation, e.g., a counter ion such as sodium or potassium to a metalate added to the hydrolysis zone to stabilize the selectivity-enhancing metalate, it may be desired to remove such cation from the alkylene glycol-containing stream. Suitable measures for recovery of cations include cation exchange resins. When, for example, a hydroxide form anion exchange resin is used to recover metalate anion (some of which is associated with, say, sodium ion), the sodium hydroxide that is formed by the exchange can be rendered innocuous by contact with a hydrogen form cation exchange resin.

In respect to the drawing, a feed mixture comprising alkylene oxide, water and water soluble metalate anion-containing material in an amount sufficient to enhance the stability of the anion exchange resin is introduced via line 10. Line 10 is in fluid flow communication with each of valves 110, 210, 310 and 410. Valve 110 is in communication with the bottom of vessel 100, valve 210 with vessel 220 and so forth, and each valve can be positioned to stop the flow of the feed mixture to the respective vessel or to allow it to pass.

As depicted, the feed mixture passes upwardly through the vessel and exits at the top. The top of each vessel is in fluid flow communication with valve 120, 220, 320 or 420, respectively. Each of these valves is in fluid communication with three other lines; line 20, a glycol reaction mixture line; line 30, a glycol product line; and line 40, a utility line.

Line 20, the glycol reaction mixture line, is in fluid flow communication with each of valves 110, 210, 310 and 410. Thus, each of these valves is capable of being positioned such that the fluid in line 20 can flow into the bottom of its respective vessel.

Line 30, the glycol product line, is the line through which the alkylene glycol product exits the system. Line 40, a utility line, can serve several purposes. It can bring, through valve 42, fluids into or out of the system. For instance, a solution containing metalate anion can be brought into the system for increasing the portion of the electropositive complexing sites on the resin that are exchanged with metalate anion. With valve 42 closed, the line becomes one which can direct fluid from one vessel to another.

Another utility line, line 50, is provided in communication with each of valves 110, 210, 310 and 410. Valve 52 is provided so that utility line 50 can be used for the ingress or egress of fluids from the system or for directed fluid from one vessel to another.

The valves can be automated to facilitate coordination of the positionings of the valves and to enable sequencing of the vessels. Each of the valves may be a single unit or they may be composed of several valves to effect the desired flow patterns, e.g., instead of one valve 110, a valve may be provided on each of lines 10, 20 and 50.

As can readily be appreciated, numerous modes of operation are permissible.

The following provides specific illustrations of the invention for purposes of understanding and is not intended to be in limitation thereof.

Apparatus:
Two stream jacketed reactors (inside diameter of 2.54 centimeters and length of about 150 centimeters) connected in series with water cooler in between. Reactors loosely packed with anion exchange resin with screens at each end.

Anion exchange resin:
Resin A: Dowex MSA-1 (TM), anionic exchange resin (available from The Dow Chemical Company) with quaternary ammonium functionality, hydroxide form, exchange capacity of about 4 meq/g (dry), 20 to 50 mesh, U.S. Sieve Series.
Resin B: The same as Resin A except chloride form and exchanged with potassium molybdate until no chloride ion detected in wash effluent.
Resin C: The same as Resin A except chloride form and exchanged with potassium tungstate until no chloride ion detected in wash effluent.

Feed Stream:
Ethylene oxide: 0.2 kilogram per hour
Water (deionized): 2 kilograms per hour Procedure:
Ethylene oxide and water are premixed at about 50° C. and introduced at about 15 atmospheres absolute into a reactor (active reactor).
Active reactor is maintained at 120° C. (initial steam heating) then water cooled once reaction initiated. Other reactor (recovery vessel) is maintained at about 50° C.
Effluent from active reactor cooled to 50° C. and introduced into recovery vessel.
Effluent withdrawn from recovery vessel and analyzed for metalate anion. At breakthrough (about 2-5 ppm by weight molybdate anion) flow pattern reversed.

The details of the operation are summarized as follows:

ILLUSTRATION 1

Start up:
First reactor filled with Resin B;
Second reactor filled with about 75 centimeters of Resin B (from reactor entrance to approximately the mid-point of the reactor) with the remainder filled with Resin A.

First cycle operation:
The feed is introduced into the first reactor. The effluent from the first reactor evidences substantially complete conversion of ethylene oxide, selectivity to monoethylene glycol about 98 percent. Metalate anion breakthrough in effluent from second reactor occurs in about 20 days at which time the second cycle is begun.

Second cycle operation:

The feed is introduced into the second reactor at the end which had contained Resin A. The effluent from the first reactor evidences substantially complete conversion of ethylene oxide, selectivity to monoethylene glycol about 97–98 percent. Metalate anion breakthrough in effluent from first reactor occurs in about 10 to 15 days and the second cycle is terminated after 15 days.

ILLUSTRATION 2

The procedure of illustration 1 is repeated except that Resin C is used instead of Resin B. Breakthrough in the first cycle operation occurs in slightly more than 20 days and the second cycle is terminated after 12 days.

It is claimed:

1. A process for the production of alkylene glycols by the hydrolysis of alkylene oxide in the presence of a selectivity-enhancing metalate anion-containing material comprising;
   (a) contacting in a hydrolysis zone the alkylene oxide and water under hydrolysis conditions sufficient to produce alkylene glycol in the presence of selectivity-enhancing amounts of metalate anion-containing material, wherein said metalate-anion containing material comprises metalate anion in association with electro-positive complexing sites on a solid and metalate anion is displaced from the electropositive complexing sites during the hydrolysis;
   (b) withdrawing an alkylene glycol-containing stream from the hydrolysis zone which alkylene glycol-containing stream contains metalate anion;
   (c) contacting the alkylene glycol-containing stream with a solid having electropositive complexing sites thereon which are in association with a replaceable anion wherein the electropositive complexing sites have a greater affinity for the metalate anion than the replaceable anion, said contacting being under conditions such that the content of the metalate anion in the alkylene glycol-containing stream is reduced and
   (d) using as at least a portion of the metalate anion-containing material in the hydrolysis zone the solid having electropositive complexing sites after contacting the alkylene glycol-containing stream to remove metalate anion therefrom.

2. The process of claim 1 wherein the solid having electropositive complexing sites after contacting the alkylene glycol-containing stream to remove metalate anion therefrom and before being used as at least a portion of the metalate anion-containing material in the hydrolysis zone is contacted with an aqueous solution containing dissolved metalate anion to increase the proportion of the electropositive complexing sites that are associated with metalate anion.

3. The process of claim 2 wherein substantially all the electropositive complexing sites are in association with metalate anion.

4. The process of claim 1 wherein water-soluble metalate anion-containing material is provided in the reaction zone in an amount sufficient to enhance the stability of the solid having electropositive complexing sites.

5. The process of claim 4 wherein the solid having complexing sites is an anion exchange resin.

6. The process of claim 5 wherein the electropositive complexing sites comprise at least one member of the group consisting of quaternary ammonium, protonated tertiary amine, and quaternary phosphonium sites.

7. The process of claim 6 wherein the replaceable anion comprises at least one member of the group of hydroxide and halogen.

8. The process of claim 4 wherein the metalate anion comprises at least one member of the group of molybdate, tungstate, metavanadate, hydrogen pyrovanadate and pyrovanadate.

9. The process of claim 8 wherein the alkylene oxide is ethylene oxide.

10. The process of claim 1 wherein the alkylene oxide has the formula:

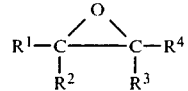

wherein $R^1$, $R^2$, $R^3$ and $R^4$ are the same or different and are hydrogen, alkyl of between 1 and 10 carbon atoms, monocyclic and bicyclic aryl having up to about 12 carbon atoms, alkaryl having about 7 to 10 carbon atoms, monocyclic or bicyclic aralkyl having 7 to about 15 carbon atoms, alkenyl having 2 or 3 carbon atoms, cycloalkyl having 3 to about 8 carbon atoms, and cyclic structures joining two or $R^1$, $R^2$, $R^3$ and $R^4$ having 3 to about 8 carbon atoms, and the metalate anion is represented by the structure:

$$[(A)_m M(O)]^{-q}$$

wherein M is a polyvalent metal atom having a positive oxidation state of at least +3, q is the negative charge of the metalate anion, and A is one or more substituents to fill the remaining valencies (m) of M and is selected from the group consisting of double-bonded oxygen and —O— wherein at least one A is —O—.

11. The process of claim 10 wherein the electropositive complexing sites are represented by the structure $$-X-(R)_n$$

wherein X is nitrogen, phosphorous, sulfur, or arsenic bonded directly or indirectly to the support, each R may be the same or different and is monocyclic aryl or aralkyl of 6 to 8 carbon atoms, monocyclic aralkyl of 7 to 9 carbon atoms, or alkyl or alkoxy of 1 to about 6 carbon atoms and n designates that sufficient R groups are provided to satisfy the remaining valencies of X.

12. The process of claim 11 wherein each R is alkyl.

13. The process of claim 12 wherein each R is methyl.

14. The process of claim 11 wherein X is attached to the solid support through an alkylene, arylene, silyl or siloxy group.

15. The process at claim 10 wherein the electropositive complexing sites comprise protonated tertiary amine.

16. The process of claim 10 wherein the electropositive complexing sites comprise quaternary phosphonium.

17. The process of claim 10 wherein the electropositive complexing sites comprise quaternary ammonium.

18. The process of claim 10 wherein the metalate anion comprises at least one member from the group of the molybdate, tungstate, metavanadate, hydrogen pyrovanadate and pyrovanadate.

19. The process of claim 18 wherein the alkylene oxide is ethylene oxide.

20. The process of claim 18 wherein the solid support comprises styrene-divinyl benzene copolymer.

21. The process of claim 10 wherein the support has about 0.5 to 5 milli-equivalents of exchange capacity per gram of dry support.

22. The process of claim 10 which is conducted on a continuous basis.

* * * * *